(12) United States Patent
Andrews et al.

(10) Patent No.: US 12,710,415 B2
(45) Date of Patent: Aug. 18, 2026

(54) APPARATUS AND METHOD FOR DIRECT NITRATE SENSING IN SOIL

(71) Applicant: Wisconsin Alumni Research Foundation, Madison, WI (US)

(72) Inventors: Joseph Andrews, Madison, WI (US); Aatresha Biswas, Hillsboro, OR (US); Jingyi Huang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 452 days.

(21) Appl. No.: 18/524,475

(22) Filed: Nov. 30, 2023

(65) Prior Publication Data

US 2025/0180537 A1 Jun. 5, 2025

(51) Int. Cl.
*G01N 33/24* (2006.01)
*G01N 27/333* (2006.01)

(52) U.S. Cl.
CPC ........... *G01N 33/24* (2013.01); *G01N 27/333* (2013.01); *G01N 33/245* (2024.05)

(58) Field of Classification Search
CPC .... A01C 21/007; G01N 27/333; G01N 33/24; G01N 33/245
See application file for complete search history.

(56) References Cited

U.S. PATENT DOCUMENTS

2015/0323491 A1* 11/2015 Miller ................ G01N 27/4035 205/789

FOREIGN PATENT DOCUMENTS

WO WO-2021245202 A1 * 12/2021 ......... G01N 27/3335
WO WO-2024263735 A1 * 12/2024 ........... A01C 21/007

OTHER PUBLICATIONS

Philippe Buhlmann et al.; "Ion-selective electrodes with ionophore-doped sensing membranes." Supramolecular Chemistry: From Molecules to Nanomaterials 5 (2012): pp. 2539 to 2579. US.
Azahar Ali et al.; "Continuous monitoring of soil nitrate using a miniature sensor with poly (3-octyl-thiophene) and molybdenum disulfide nanocomposite." ACS applied materials & interfaces 11, No. 32 (2019): pp. 1-38; US.
Baumbauer et al.; "Printed Potentiometric Nitrate Sensors for Use in Soil." Sensors 22, No. 11 (2022): pp. 1 to 13; US.

* cited by examiner

*Primary Examiner* — Jennifer Wecker
(74) *Attorney, Agent, or Firm* — Boyle Fredrickson, S.C.

(57) ABSTRACT

A soil chemistry sensor employs a hydrophilic porous layer to adapt aqueous ion sensors to direct soil measurement by allowing transfer and concentration of water from the soil to the sensing electrodes while blocking electrically charged soil colloidal particles that can interfere with such measurements.

15 Claims, 3 Drawing Sheets

APPARATUS AND METHOD FOR DIRECT NITRATE SENSING IN SOIL

STATEMENT REGARDING FEDERALLY SPONSORED RESEARCH OR DEVELOPMENT

This invention was made with government support under 2022-67019-36268 awarded by the USDA/NIFA. The government has certain rights in the invention.

CROSS REFERENCE TO RELATED APPLICATION

Background of the Invention

The present invention relates generally to sensors for making direct measurements of soil chemistry, for example, in the form of nitrate or phosphate concentrations.

Nitrate is an essential nutrient for maintaining crop productivity and achieving high yields for regional and global food security. However, excess nitrate from fertilization can be harmful to local environments through a process called nitrate leaching. In this process, negatively charged nitrate ions $$(NO_3^-)$$

leave the soil and enter the groundwater, polluting drinking water and aquatic systems.

Nitrate measurements using farm soil sampling and laboratory analysis can provide useful information about the nitrate status for managing the application of fertilizer to reduce nitrate leaching. Such techniques collect a volume of soil and extract the nitrates into a solution which may then be analyzed using conventional aqueous test methods. One such test method is open-circuit potentiometry which relies on a voltage difference developed between two electrodes across an ion selective membrane (ISM). This voltage can be used to determine a nitrite or similar ion concentration according to the Nernst equation.

Such soil-sampling methods are costly and cumbersome and, in this respect, are not well adapted to real time nitrate monitoring. Preferably, the direct measurement of soil chemistry could be determined, for example, by long-term installation of a probe into the soil that can make continuous measurements. Such probes have been developed using potentiometric techniques, but suffer from complex fabrication processes or the need for extremely wet soil.

SUMMARY OF THE INVENTION

The present invention provides a sensor for direct measurements of soil chemistry employing a hydrophilic porous layer that serves to adapt aqueous potentiometric measurement techniques to the dryer soil environment. The porous nature of the hydrophilic film conducts water in from the soil to the aqueous potentiometric sensor while blocking microscopic, charged soil particles (soil colloids) that can interfere with the electrical measurements. The result is a sensor that allows direct, dynamic measurements of ion concentration in a range of soil types with stabilization times of a few hours or less, making low-cost, real-time monitoring practical.

In one example, the invention provides a soil chemistry sensor having a support adapted for insertion into the soil. A working electrode and reference electrode are held in separation on the support, and an ion selective membrane is positioned over the working surface of the working electrode to selectively pass an ion species of interest. A hydrophilic porous barrier layer is positioned over the ion selective membrane of the working surface and the reference electrode allowing aqueous communication of water from the soil to the working electrode and reference electrode while blocking charged soil particles. The hydrophilic porous barrier layer allows passage of the ion species of interest for measurement of concentrations of the ion species of interest in the soil according to a voltage between the reference electrode and working electrode.

It is thus a feature of at least one embodiment of the invention to adapt aqueous sensor technology to drier soil conditions through the use of a porous barrier layer that can draw in water from the soil while blocking charged soil particles.

The hydrophilic porous barrier layer may operate to allow identification of a Nernst potential asymptote within three hours to within 10 mV.

It is thus a feature of at least one embodiment of the invention to provide a barrier that accommodates sufficient transfer of water and ionic species between the soil and the sensor electrodes to provide accurate dynamic measurements.

The ion selective membrane may be an ion selective membrane for nitrate or phosphate.

It is thus a feature of at least one embodiment of the invention to provide a system well adapted to common aqueous sensing technologies useful for analysis of soil conditions.

The reference electrode and working electrode may be silver/silver chloride electrodes.

It is thus a feature of at least one embodiment of the invention to provide a low-cost but stable electrode adapted to a variety of fabrication techniques.

The soil chemistry sensor may further include a moisture sensor and a temperature sensor.

It is thus a feature of at least one embodiment of the invention to provide a more complete picture of soil environment and to assist in compensating for temperature effects in the calculation of concentration of the ion species of interest from the measured voltage.

These particular objects and advantages may apply to only some embodiments falling within the claims and thus do not define the scope of the invention.

DETAILED DESCRIPTION OF THE PREFERRED EMBODIMENT

Figure 1:
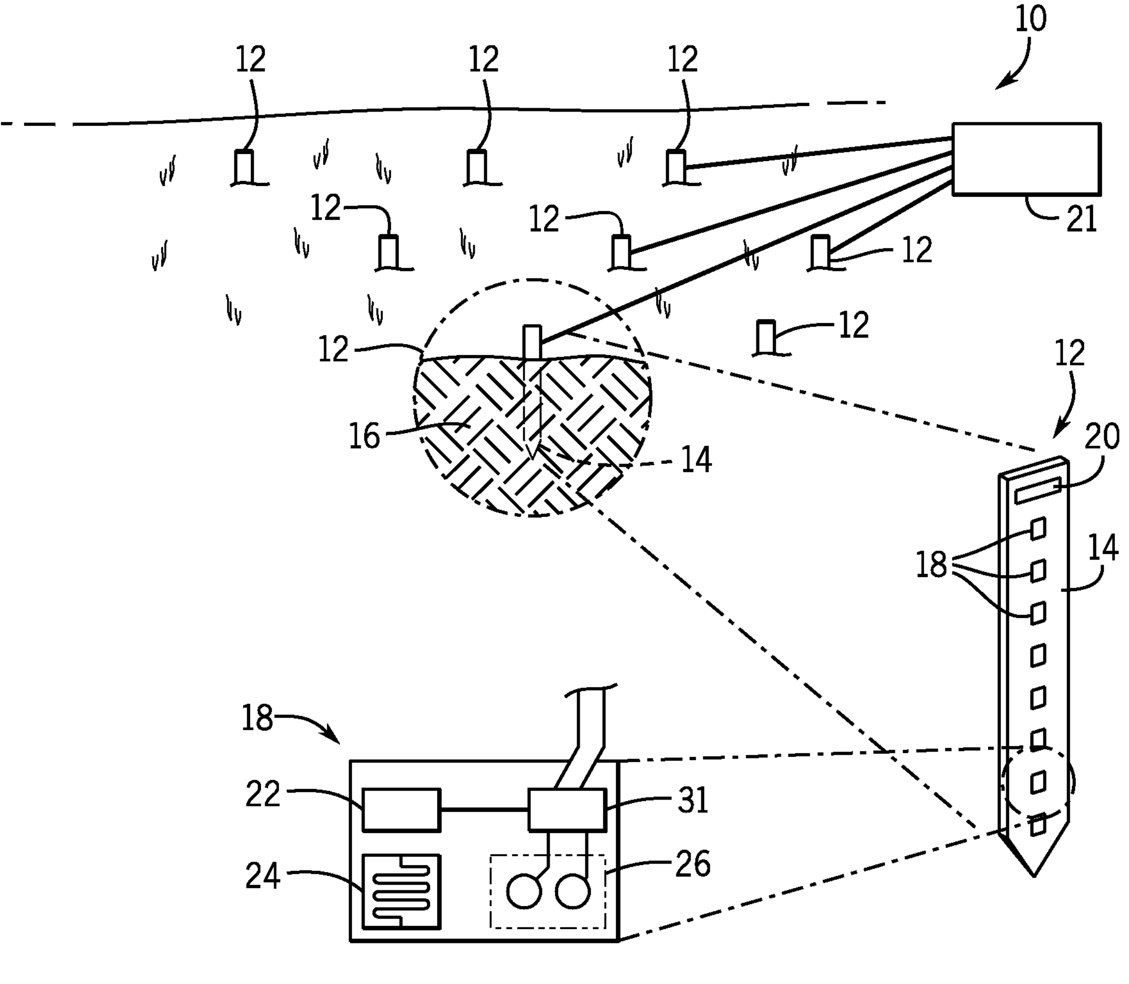
FIG. 1 is a simplified perspective view of an agricultural field such as may provide a set of sensor arrays at different locations for monitoring soil conditions, and shows an embodiment in which each sensor provides multiple sensor elements positioned at different heights for making measurements at different soil depths, each sensor element including a nitrate, moisture, and temperature sensor.

Referring now to FIG. 1, a soil chemistry monitoring system 10 may provide a set of sensor arrays 12 in the form of stakes 14 that may be inserted into the soil 16 at regular locations, for example, in a grid, to monitor soil conditions at those locations. The stakes 14 may remain in position for an extended duration to allow long-term diffusion of materials such as nitrates to be tracked over time.

For this purpose, a lower portion of each stake 14 may expose a set of sensor elements 18 spaced vertically along one face of the stake 14 to be in direct contact with the soil 16. An upper end of each stake 14 may include shared circuitry 20 communicating with each sensor element 18 to receive data from the sensor elements 18 and to provide power to the sensor elements 18. The power provided to the sensor elements 18 may be from a battery source or solar panel or the like.

The shared circuitry 20 may further provide a communication link, for example, using a radio mesh network, to transmit readings of soil chemistry collected by each sensor element 18 and each sensor array 12 to a central station 21. The soil chemistry information collected by each sensor array 12 will be identified to the sensor array 12 (and hence its location in a field) and the particular sensor element 18 (and hence the depth of the measurement) to provide a three-dimensional array of measurements on regular time intervals, for example, 1 to 2 hours.

The central station 21 may provide data logging circuitry or a long-range transmitter for forwarding this be information to a remote station for analysis. Such analysis may include generating a two-dimensional map of nitrate diffusion over time.

Referring still to FIG. 1, in one embodiment, each sensor element 18 may include a temperature sensor 22, a soil moisture sensor 24, and a nitrate or potassium sensor 26 which may provide separate measurements of these sensed quantities for each sensor element 18.

The temperature sensor 22 and soil moisture sensor 24 may make use of standard circuits for this purpose, for example, the temperature sensor 22 being a solid-state semiconductor temperature sensor, a resistance temperature detector (RTD), a thermocouple, or thermistor. In one embodiment, the moisture sensor may deduce soil moisture content by making measurements of the soil electrical dielectric in the vicinity of the element 18, for example, by monitoring a change in a capacitance including the soil dielectric and forming part of the oscillator circuit whose frequency is affected by dielectric. Using a measurement of this frequency, a volumetric measurement of soil moisture can be obtained not limited to moisture immediately adjacent to the sensor element 18.

Figure 2:
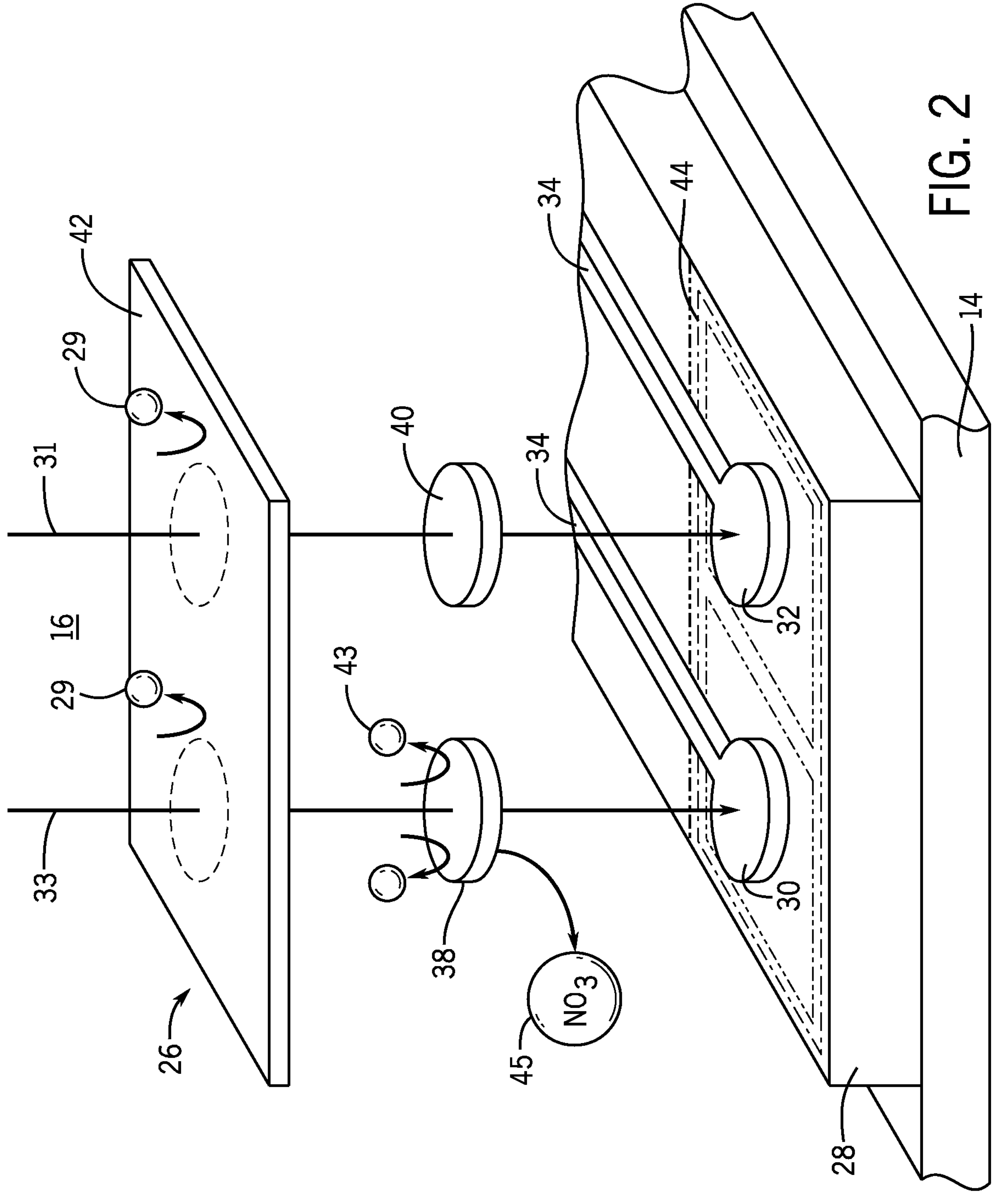
FIG. 2 is an exploded perspective view the nitrate sensor of FIG. 2 providing open-circuit potentiometric sensor electrodes positioned behind a hydrophilic porous film adapting the sensor electrodes to soil conditions.

Referring now to FIGS. 1 and 2, the nitrate sensor 26 may be specially constructed to provide direct measurements of the soil 16. In one embodiment the nitrate sensor 26 is attached to the stake 14 via an insulating substrate, for example, an adhesive polyimide film, such as is commercially available under the trade name of Kapton®. The exposed side of the substrate 28 may support a working electrode 30 and a reference electrode 32, for example, displaced horizontally with respect to the vertical displacement of sensor elements 18. Each of the working electrodes 30 and reference electrode 32 have independent connecting leads 34 to conduct voltages on those electrodes to a high impedance multiplexer/analog-to-digital converter (MUX A/D) 36. The MUX A/D 36 may provide for a high-impedance input, for example, using MOS transistors to selectively receive signals in a multiplex fashion from the nitrate sensor 26, the temperature sensor 22 and moisture sensor 24. This high-impedance input allows the MUX A/D 36 to implement an open-circuit measurement of the voltage between the working electrodes 30 and reference electrode 32.

In one embodiment, the working electrode 30, the reference electrode 32, and leads 34 may be a nonreactive conductive material, for example, gold or a gold-plated conductor; however, in the preferred embodiment, the working electrode 30, the reference electrode 32, and leads 34 are a combination of silver and silver chloride to provide a so-called AG/AgCl electrode which provides an electrochemically stabilized voltage measurement point. The working electrode 30, reference electrode 32, and leads 34 may be printed on the substrate 28, for example, by additive printing, sputtering or other techniques.

An ion selective membrane (ISM) 38 covers the exposed surface of the working electrode 30 to preferentially permit the passage of water 33 and a desired chemical species (in this case aqueous nitrate anions 45) and to reject anions 41 of different chemical species and cations 43, for example, environmentally associated with the nitrate anions 45 outside of the ISM 38.

This migration of the nitrate anions 45 produces a net electrical potential across the ISM 38 at which equilibrium is described by the Nernst potential:

$$E_{membrane} = \frac{RT}{zF}\ln\frac{[\text{ion}]_{out}}{[\text{ion}]_{in}}$$

where $E_{membrane}$ is the potential across the ISM 38 created by the separation of anions and cations (measured in volts), R is the universal gas constant (in joules per kelvin per mole), T is the absolute temperature (in kelvin), F is Faraday's constant (which represents the number of coulombs of charge per mole of electrons), z is the charge on the ion species of interest $$(NO_3^-$$

in this example), $[\text{ion}]_{out}$ is the concentration of the ion species of interest outside the ISM 38 (toward the soil) and $[\text{ion}]_{in}$ is the concentration of the ion species of interest and inside the ISM 38 (toward working electrode 30).

As noted, this Nernst potential (voltage) may be measured by the MUX A/D 36 between the working electrode 30 and the reference electrode 32. A temperature measured by the temperature sensor 22 described above may be used as part of the calculation of the Nernst potential which then yields a concentration measurement.

The reference electrode 32 provides a reference point for measurement on the soil side of the membrane 38 without an ISM 38 that would generate a Nernst potential by selectively passing nitrate anions 45. To the contrary, and for improved durability, the reference electrode 32 may be covered with an anion-blocking membrane 40, for example, of a sulfonated tetrachloroethylene-based fluoropolymer-copolymer commercially available under the trade name Nafion™. This anion-blocking membrane 40 serves to reduce erosion of the reference electrode 32 from leaching of the silver chloride anion (when a silver/silver chloride reference electrode is used) into the environment.

The working electrode 30 with the ISM 38 and the reference electrode 32 with the anion-blocking membrane 40 are covered by a hydrophilic porous sheet 42, for example, a Polyvinylidene Fluoride (PVDF) membrane having a pore size of less than 1 μm. The hydrophilic porous sheet 42 allows for the passage of water 30 but blocks charged soil particles 29 that would unfavorably affect the sensitive electrical measurements to be made. The hydrophilic porous sheet 42 may provide a water contact angle of less than 60° following the convention that water contact angle is measured from a horizontal plane to a tangent of the outer surface of the water drop of the periphery of a water droplet from the side of the tangent toward the water droplet. Preferably, the hydrophilic porous sheet 42 may exhibit a change (decreasing) in water contact angle of greater than 30° per second.

A hydrophilic porous sheet 42 suitable for use with the present invention is commercially available under the trade name of Immobilon-E transfer membranes (product number IEVH07804), obtained from Merck Millipore Ltd, with a pore size of 0.45 um The hydrophilic porous sheet 42 in some embodiments may be further treated, for example, by immersion in a solution containing 10 mL of 4 mg/mL catechol and 10 mL of 5 mg/mL of sodium perodate to increase this hydrophilic property, for example, as may be desired for dryer soil conditions.

The hydrophilic porous sheet 42 is adhered at peripheral regions 44 around the working electrode 30 and ISM 38 and reference electrode 32 and anion blocking membrane 40 to isolate these elements from communication with the external soil 16 along paths other than through the hydrophilic porous sheet 42. The peripheral regions 44 also serve to separate the working electrode and ISM 38 from direct communication with the reference electrode 32 and anion blocking membrane 40 except by passage of material through the hydrophilic porous sheet 42.

Figure 3:
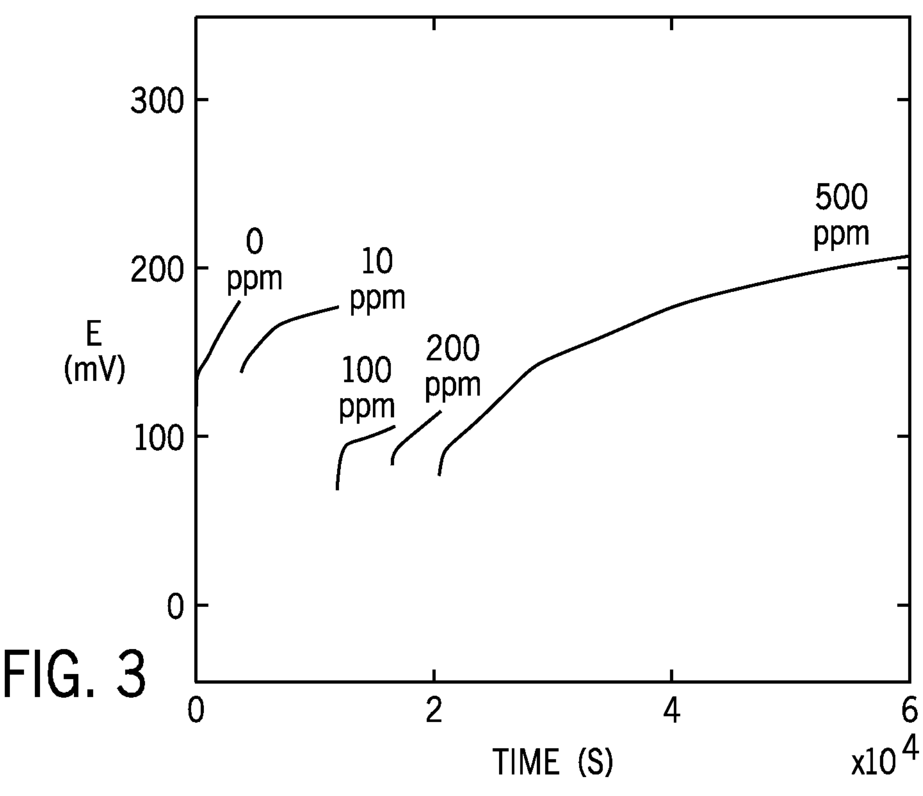
FIGS. 3 and 4 are plots of measured voltage between the sensor electrodes over time showing measured voltage for different concentrations of nitrates in soil with and without the hydrophilic porous film of FIG. 2.
Figure 4:
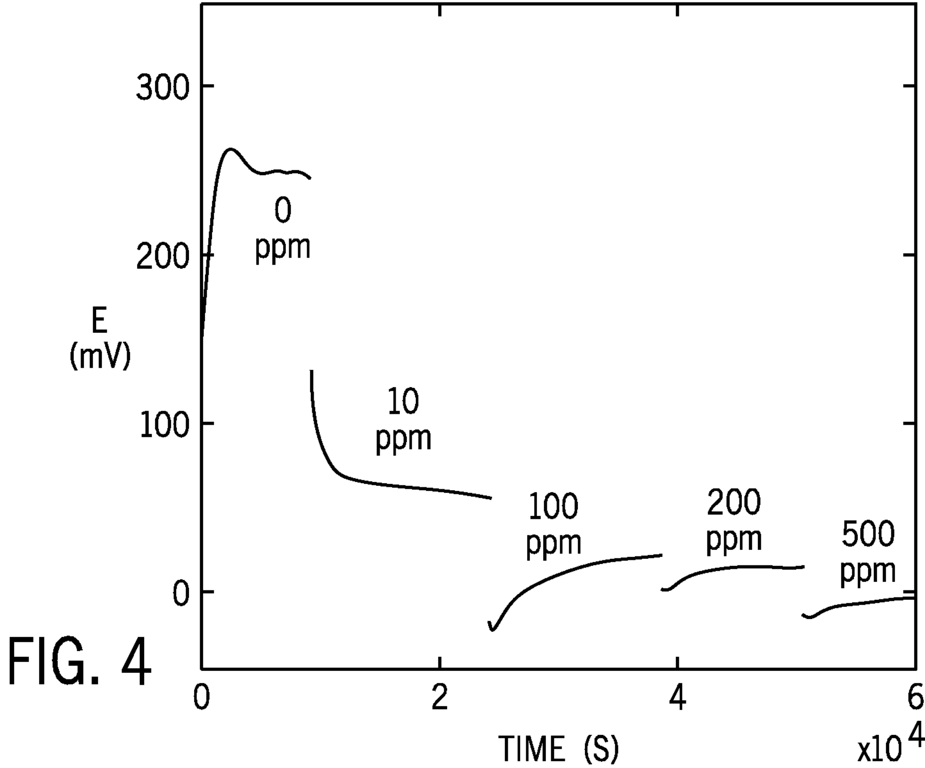

Referring now to FIGS. 3 and 4, experimental measurements of the nitrate sensor 26 in soil samples at various concentrations of $$NO_3^-$$

without the hydrophilic porous sheet 42 (shown in FIG. 3) and with the hydrophilic porous sheet 42 (shown in FIG. 4) show the significant contribution of the hydrophilic porous sheet 42 in producing stable measurements of Nernst potential (the vertical axis) and reveal asymptotes within the space of a few hours and provide distinct bands of ranges of measured Nernst potentials with a resolution of less than 10 mV to reveal concentration of $$NO_3^-.$$

Generally the properties and dimensions of the present invention will be adjusted to provide accurate determination of the asymptote of the Nernst potential to within 10 mV in less than three hours.

Potentiometric Sensor Fabrication

One embodiment of fabrication of the present invention will now be described.

In this embodiment, the working electrode 30, reference electrode 32, and leads 34 are fabricated using the inkjet Dimatix Materials (DMP-2850) printer with a 1-pL (picoliter) printhead and silver nanoparticle ink (Ag NP) procured from Novacentrix Inc. The Dimatrix Materials printer uses a piezoelectric printed head to deposit silver nanoparticle ink. The substrate 28 is a polyimide (Kapton) with a thickness of 128 micrometers procured from McMaster-Carr and selected because of its flexibility and thermal resilience. This substrate has a temperature range from −268° C. to 399° C. which allows for sintering of the silver nanoparticle ink after deposition to form conductive traces.

The printing process included depositing two layers of ink for each of the sensors for high conductivity of the silver traces. The printed electrodes were sintered at 260° C. for one hour. Acrylic is applied on the leads 34 to passivate the leads 34 outside of the working electrode 30 and reference electrode 32.

After passivation, the silver (Ag) of the working electrode 30 and reference electrode 32 electrodes are converted into silver/silver chloride (Ag/AgCl) electrodes through incubation in commercial bleach containing 6% sodium hypochlorite. The commercially available bleach is diluted with water to make a 0.06% solution by volume. The printed electrodes are immersed in 0.06% (v/v) bleach solution for 5 seconds and are immediately rinsed with deionized (DI) water. This process leads to the formation of Ag/AgCl electrodes which are relatively more stable than silver (Ag) electrodes.

For formation of the anion blocking membrane 40 of the reference electrodes 30, 12 microliters of Nafion are drop cast on the Ag/AgCl reference electrode 32.

The printed sensor is then sintered at 140° C. in vacuum conditions. The Nafion layer prevents chloride (Cl—) leaching from the working reference electrode 32 in soil conditions.

Creation of the ion specific ISM 38 on the working electrode 30 is provided by mixing 1 ml of tetrahydrofuran, 64 μl of 2-nitrophenyl octyl ether, 32 mg of polyvinyl chloride (PVC), and 4 mg of tetradodecylammonium nitrate (TDAN) obtained from Sigma Adrich. Twelve pl of the prepared solution is drop cast on the Ag/AgCl surface of the working electrode 30 with the help of a pipette. The sensor is then left at room temperature for about 24 hours for the solution to dry and form a film on the working electrode.

After anion blocking membrane 40 and ISM 38 are applied respectively to the reference electrode 32 and working electrode 30, this assembly is immersed in a 0.01M $KNO_3$ solution for the conditioning treatment. The solution is prepared by dissolving $KN0_3$ in deionized water. The sensors are then conditioned in 0.01M potassium nitrate $KNO_3$ solution for 12-13 hours. Additional details on constructing sensors of this type are found, for example, at Elena Zdrachek and Eric Bakker, Potentiometric sensing, Analytical chemistry, 91(1):2-26, 2018, hereby incorporated by reference.

Finally the hydrophilic porous sheet 42 was attached to the substrate as discussed above.

While the present invention has been described with respect to the measurement of nitrates in the soil, it will be appreciated that this system of employing a hydrophilic porous membrane to convert aqueous, ion-sensing electrode systems to use with direct contact in the soil can be employed with other ion species susceptible to aqueous analysis, for example, phosphates, by adjustment of the ISM 38.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. A soil chemistry sensor comprising:

a support adapted for insertion into the soil;

a working electrode and reference electrode held in separation on the support;

an ion selective membrane positioned above the working surface of the working electrode and configured to selectively pass an ion species of interest through the ion selective membrane; and a hydrophilic porous barrier layer positioned above the ion selective membrane of the working surface and the reference electrode, said hydrophilic porous barrier layer configured for allowing aqueous communication of water from the soil to the working electrode and reference electrode when the support is inserted into the soil while blocking charged soil particles, the hydrophilic porous barrier layer configured to allow passage of the ion species of interest for measurement of concentrations of the ion species of interest in the soil according to a voltage across the reference electrode and working electrode.

2. The soil chemistry sensor of claim 1 wherein the hydrophilic porous barrier has an average pore size of less than 1 μm and a water contact angle of less than 70°.

3. The soil chemistry sensor of claim 2 wherein the hydrophilic porous barrier provides a water contact angle that decreases at greater than 30° per second.

4. The soil chemistry sensor of claim 1 wherein the hydrophilic porous barrier is polyvinylidene fluoride.

5. The soil chemistry sensor of claim 1 wherein the hydrophilic porous barrier is less than 20 μm thick.

6. The soil chemistry sensor of claim 1 wherein the voltage between the reference electrode and working electrode provide a measure of a Nernst potential across the ion selective membrane.

7. The soil chemistry sensor of claim 1 wherein the hydrophilic porous barrier layer blocks soil particles while allowing aqueous transmission of the ion species of interest sufficient to identify a Nernst potential asymptote within three hours to within 10 mV.

8. The soil chemistry sensor of claim 1 wherein the porous barrier layer is sealed to the support at a periphery of the porous barrier layer to encapsulate the working electrode and reference electrode.

9. The soil chemistry sensor of claim 1 wherein the ion selective membrane is selected from the group consisting of ion selective membranes for the group consisting of nitrate and phosphate.

10. The soil chemistry sensor of claim 1 wherein the voltage may distinguish concentrations of the ion species of interest in a range from 0 to 500 ppm with 10 millivolt accuracy.

11. The soil chemistry sensor of claim 1 wherein the reference electrode and working electrode are silver/silver chloride electrodes.

12. The soil chemistry sensor of claim 1 further including moisture sensor and temperature sensor.

13. The soil chemistry sensor of claim 1 wherein the support holds multiple separated sensor elements each comprised of:

a working electrode and reference electrode held in separation on the support;

an ion selective membrane positioned over the working surface of the working electrode to selectively pass an ion species of interest;

a hydrophilic porous barrier layer positioned over the ion selective membrane of the working surface and the reference electrode allowing aqueous communication of water from the soil to the working electrode and reference electrode when the support is inserted into the soil while blocking charged soil particles, the hydrophilic porous barrier layer adapted to allow passage of the ion species of interest for measurement of concentrations of the ion species of interest in the soil according to a voltage between the reference electrode and working electrode; and wherein the sensor elements are arrayed to detect soil chemistry at different depths within the soil when the support is inserted into the soil.

14. A method of making direct soil chemistry measurements comprising:

(a) installing a soil chemistry sensor into soil to be measured, the soil chemistry sensor having: a support adapted for insertion into the soil; a working electrode and reference electrode held in separation on the support; an ion selective membrane positioned above the working surface of the working electrode to selectively pass an ion species of interest through the ion selective membrane; and a hydrophilic porous barrier layer positioned above the ion selective membrane of the working surface and the reference electrode allowing aqueous communication of water from the soil to the working electrode and reference electrode when the support is inserted into the soil while blocking charged soil particles, the hydrophilic porous barrier layer adapted to allow passage of the ion species of interest from the soil to the reference electrode and working electrode; and (b) measuring a voltage across the reference electrode and working electrode to determine a concentration of the ion species of interest.

15. The method of claim 14 wherein the hydrophilic porous barrier has an average pore size of less than 1 μm and a water contact angle of less than 70°.

* * * * *